(12) United States Patent
Fenton et al.

(10) Patent No.: US 9,642,995 B2
(45) Date of Patent: May 9, 2017

(54) EXTERNAL NASAL DILATOR

(75) Inventors: Gustav R. Fenton, Minneapolis, MN (US); Snigdha Mishra, Parsippany, NJ (US)

(73) Assignee: GlaxoSmithKline, LLC, Wilmington, DE (US)

( * ) Notice: Subject to any disclaimer, the term of this patent is extended or adjusted under 35 U.S.C. 154(b) by 0 days.

(21) Appl. No.: 13/389,656

(22) PCT Filed: Dec. 21, 2010

(86) PCT No.: PCT/US2010/061399
§ 371 (c)(1),
(2), (4) Date: Mar. 1, 2012

(87) PCT Pub. No.: WO2011/079088
PCT Pub. Date: Jun. 30, 2011

(65) Prior Publication Data
US 2012/0172923 A1    Jul. 5, 2012

Related U.S. Application Data

(60) Provisional application No. 61/289,465, filed on Dec. 23, 2009.

(51) Int. Cl.
*A61M 29/00* (2006.01)
*A61F 5/08* (2006.01)

(52) U.S. Cl.
CPC ............... *A61M 29/00* (2013.01); *A61F 5/08* (2013.01); *A61M 2210/0618* (2013.01)

(58) Field of Classification Search
CPC . A61F 5/08; A61F 5/56; A61M 29/00; A61M 2210/0618
USPC ....... 606/199, 204, 204.45; 128/200.24, 207, 128/18, 207.13; 602/902
See application file for complete search history.

(56) References Cited

U.S. PATENT DOCUMENTS

| | | | |
|---|---|---|---|
| 2,471,088 A | 5/1949 | Ayre | |
| D196,412 S | 9/1963 | Ayre | |
| D210,757 S | 4/1968 | Michel | |
| D220,593 S | 4/1971 | Burnhill | |
| 5,533,499 A | 7/1996 | Johnson | |
| 5,533,503 A * | 7/1996 | Doubek et al. | 128/200.24 |
| 5,546,929 A | 8/1996 | Muchin | |
| 5,611,333 A | 3/1997 | Johnson | |
| D379,513 S | 5/1997 | Ierulli | |
| 5,653,224 A | 8/1997 | Johnson | |
| 5,718,224 A | 2/1998 | Muchin | |

(Continued)

FOREIGN PATENT DOCUMENTS

| | | |
|---|---|---|
| EP | 0842646 | 5/1998 |
| EP | 0855175 | 7/1998 |

(Continued)

OTHER PUBLICATIONS

U.S. Appl. No. 29/352,649, filed Dec. 23, 2009, Brogden et al.

(Continued)

*Primary Examiner* — Katrina Stransky
(74) *Attorney, Agent, or Firm* — Joshua C. Sanders (57) ABSTRACT

The present invention relates to an external nasal dilator, more specifically to an improved external nasal dilator, which provides a focused and efficient spring force to the outer wall tissues of a first and second nasal passages.

4 Claims, 6 Drawing Sheets (56) References Cited

U.S. PATENT DOCUMENTS

| | | |
|---|---|---|
| 5,769,089 A | 6/1998 | Hand et al. |
| 5,961,537 A | 10/1999 | Gould |
| 6,029,658 A | 2/2000 | De Voss |
| D422,358 S | 4/2000 | Lundy et al. |
| 6,065,470 A | 5/2000 | Van Cromvoirt et al. |
| D429,332 S | 8/2000 | Ierulli |
| D430,295 S | 8/2000 | Ierulli |
| 6,098,616 A | 8/2000 | Lundy, Jr. et al. |
| D432,652 S | 10/2000 | Ierulli |
| 6,318,362 B1 | 11/2001 | Johnson |
| 6,453,901 B1* | 9/2002 | Ierulli .................... 128/200.24 |
| 6,631,714 B2 | 10/2003 | Von Duyke et al. |
| D490,897 S | 6/2004 | Ruch |
| 6,769,429 B1* | 8/2004 | Benetti .................... 128/200.24 |
| 7,067,710 B1 | 6/2006 | Beaudry |
| 7,114,495 B2 | 10/2006 | Lockwood, Jr. |
| 8,182,505 B2 | 5/2012 | Blach et al. |
| 8,529,594 B2 | 9/2013 | Blach et al. |
| 2001/0032645 A1 | 10/2001 | Cronk et al. |
| 2007/0255309 A1* | 11/2007 | Guyuron et al. ............. 606/199 |
| 2008/0058858 A1 | 3/2008 | Smith |
| 2008/0184995 A1 | 8/2008 | Ierulli |
| 2008/0257341 A1* | 10/2008 | Ierulli .................... 128/200.24 |
| 2009/0234383 A1 | 9/2009 | Ierulli |

FOREIGN PATENT DOCUMENTS

| | | |
|---|---|---|
| WO | WO99/22678 | 5/1999 |
| WO | WO2005/020845 | 3/2005 |

OTHER PUBLICATIONS

U.S. Appl. No. 29/352,646, filed Dec. 23, 2009, Brunner et al.
U.S. Appl. No. 29/352,630, filed Dec. 23, 2009, Brogden et al.
U.S. Appl. No. 14/088,768, filed Nov. 25, 2013.
U.S. Appl. No. 14/012,282, filed Aug. 29, 2013.

\* cited by examiner

EXTERNAL NASAL DILATOR

RELATED APPLICATIONS

This application is a 371 of International Application No. PCT/US2010/061399, filed Dec. 21, 2010, which claims the benefit of U.S. Provisional Application No. 61/289,645, filed Dec. 23, 2009, which is incorporated herein in its entirety.

TECHNOLOGY FIELD

The present invention relates to an external nasal dilator, more specifically to an improved external nasal dilator, which provides a focused and efficient spring force to the outer wall tissues of a first and second nasal passages.

BACKGROUND

Nasal dilators, both internal and external, which act on the outer wall tissues of the nasal passages, are well known. For example, external nasal dilators are disclosed in U.S. Pat. Nos. 5,533,499, 5,533,503 and 6,318,362 to Johnson. These nasal dilators comprise a truss member having a first end region adapted to engage the outer wall tissues of a first nasal passage and a second end region adapted to engage the outer wall tissues of a second nasal passage. The first and second end regions are coupled to one another by an intermediate segment. The intermediate segment is configured to traverse a portion of the nose located between the first and second nasal passages. A resilient element or spring member extends along the length of the truss member. The spring member, when the truss is secured in place, acts to stabilize the outer wall tissue and thereby prevent the outer wall tissue of the first and second nasal passages from drawing in during breathing.

In one known nasal dilator embodiment, such as disclosed in U.S. Pat. No. 6,318,362, the resilient element may consist of a pair of resilient bands. The first resilient band is secured to run along the length of the nasal dilator truss member. The second resilient band is spaced apart from the first resilient band and is also secured to run along the length of the nasal dilator truss member. The first and second bands are relatively stiff and are oriented generally parallel to one another and substantially parallel to the longitudinal extent of the nasal dilator. The resiliency of the first and second bands prevents the outer wall tissues of the first and second nasal passages from drawing in during breathing.

While great strides have been made in understanding basic external nasal dilation, further improvements are needed. Less force to obtain similar dilation, more efficacious adhesive elements or novel dilation forces are potential areas of opportunity for improvement. Up to this point the majority of nasal dilators have exerted force either in a direction orthogonal to the lateral wall of the nose or parallel to the bridge of the nose. In this invention, significant force in a new direction is defined for nasal dilation, providing for novel force distributions on the nose to improve dilation.

SUMMARY

The external nasal dilator of the present invention comprises a truss member including a flexible strip of base material and a resilient band. The truss defines a first end region adapted to engage the outer wall tissues of a first nasal passage and a second end region adapted to engage the outer wall tissues of a second nasal passage. The first and second end regions are coupled to one another by an intermediate segment. The intermediate segment is configured to traverse a portion of the nose located between the first and second nasal passages. A resilient band extends along the entire length of the truss member. The truss is slotted inwardly from both lateral ends, terminating short of the intermediate segment. The slots divide the truss into four segments or branches. The upper and lower branches are substantially parallel to each other and the upper branches can be shorter than the lower branches. These four resilient branches can be placed independently on the user's nose so that the user can tailor the location of the force to maximize efficacy and comfort. Thus, the four resilient branches can act in unison or independently to effect nasal dilation with the upper branches acting on the left and right lateral cartilage and the lower branches acting on the left and right alar cartilages. Each of the four resilient branches is secured by an extended tab on one edge (secured above on the upper branch and secured below on the lower branch). The edge on the slot side of the resilient branch will lift significantly away from the nose as it is not secured by an extended tab design. Thus, the combination of extending the resilient band to the end of the truss, dividing the truss into four resilient branches and securing only one edge of each of the four branches to the lateral wall of the nose (with the extended tab) directs the spring forces both outward (i.e., orthogonal to the surface of the lateral wall of the nose) and upward toward the bridge of the nose. This combination of outward and upward forces leads to a more efficacious nasal dilator.

DETAILED DESCRIPTION

The nasal dilators of the present invention comprise a truss member including a flexible strip of base material and a resilient band. The truss defines a first end region and a second end region coupled to the first end region by way of an intermediate segment. The flexible strip of base material may be formed of any suitable fabric or plastic film material.

An adhesive material may be placed on one side of the truss member such that the nasal dilator may be removably affixed to the nose of a user. In one embodiment of the invention the adhesive is attached to a first side of the truss and the resilient band is attached to the second side of the truss such that the flexible strip of base material is in direct contact with the skin. The adhesive material is a pressure sensitive biocompatible adhesive that is compatible with the skin of the user but strong enough that it can maintain the nasal dilator in the correct position during use. Suitable adhesives for use in the present invention include but are not limited to solvent or water-based pressure-sensitive adhesives, such as acrylate adhesives, thermoplastics "hot melt"

adhesives, double-sided adhesive tapes, elastomer-based adhesives and acrylic adhesives. Optionally a release liner may be used to protect the pressure sensitive adhesive in transit and prior to use which can be readily removed from the adhesive material.

The truss member may further include a flexible strip of backing material so that the resilient band is disposed between the layer of backing material and the flexible strip of base material. The flexible strip of backing material may be made of rubber, vinyl, cloth, soft plastic or any other material known in the art to be pliable under the conditions for which the nasal dilator is to be used. The backing material may be the same size and shape as the base material.

Those of skill in the art will recognize that all the materials used to make the truss member must withstand the forces placed thereon and will also withstand potentially deleterious conditions, objects and materials that the nasal dilator will come in contact with, i.e. water, sweat, skin oils, etc.

The resilient band is fixedly attached to or integrated within the truss member. The resilient band is secured to run along the entire length of the nasal dilator truss member. The resilient band may be formed of a variety of polymeric materials and other materials that have a tendency to return to a normally planar state upon the removal of an external bending force. For example, industrial grade biaxially oriented polyester about 0.33 millimeters (mm) in thickness is suitable for use in the present invention. Thicknesses of 0.25 mm (0.010 inches or 10 mils) and 0.33 mm (0.013 inches or 13 mils) are currently commercially available. Thicknesses ranging from 0.13 mm (0.005 inches or 5 mils) to 0.46 mm (0.018 inches or 18 mils) could be used in this device.

Materials suitable for use in the nasal dilator of the present invention include any formable material. Such materials include, but are not limited to, thermoplastic polymeric materials like acrylonitrile-butadiene-styrene (ABS), polyethylenes including high density polyethylene (HDPE), low density polyethylene (LDPE) and high molecular weight polyethylene (HMWPE), polypropylene, polyesters including polyethylene terephthalate (PET) and glycolised polyethylene terephthalate (PETG), polystyrene, polyurethane, vinyl, linoleum, rubber compounds, acrylics, nylon compounds, corn derivatives or other biodegradable resins, such as polylactic acid and polyhydroxyalkanoates, combinations of any of the foregoing, and the like.

The truss is slotted inwardly from both lateral ends, terminating short of the intermediate segment. The two slots are of equal lengths and divide the truss into four branches that extend from the intermediate segment. Thus, the nasal dilator has two upper resilient branches and two lower resilient branches. The upper and lower branches are substantially parallel to each other. The two upper resilient branches in combination with the adjacent intermediate segment of the truss form the upper resilient element. The two lower resilient branches in combination with the adjacent intermediate segment of the truss form the lower resilient element. The length of the lower resilient element is from 35 mm to 65 mm in length, preferably 45 mm to 60 mm in length. The upper and lower resilient elements can be of the same or of different lengths, with the upper resilient element being up to 30% shorter than the lower resilient element. In one embodiment, the upper resilient element could be as long as the lower resilient element. In another embodiment, the upper resilient element could be 15% shorter than the lower resilient element. Thus the range of the ratio of the length of the upper resilient element to the lower resilient element is 70% to 100%. The overall spring force of the resilient band of a nasal dilator of the present invention is between 5 g and 50 g of force. In another embodiment the overall spring force is 18 g to 28 g of force.

Figure 1:
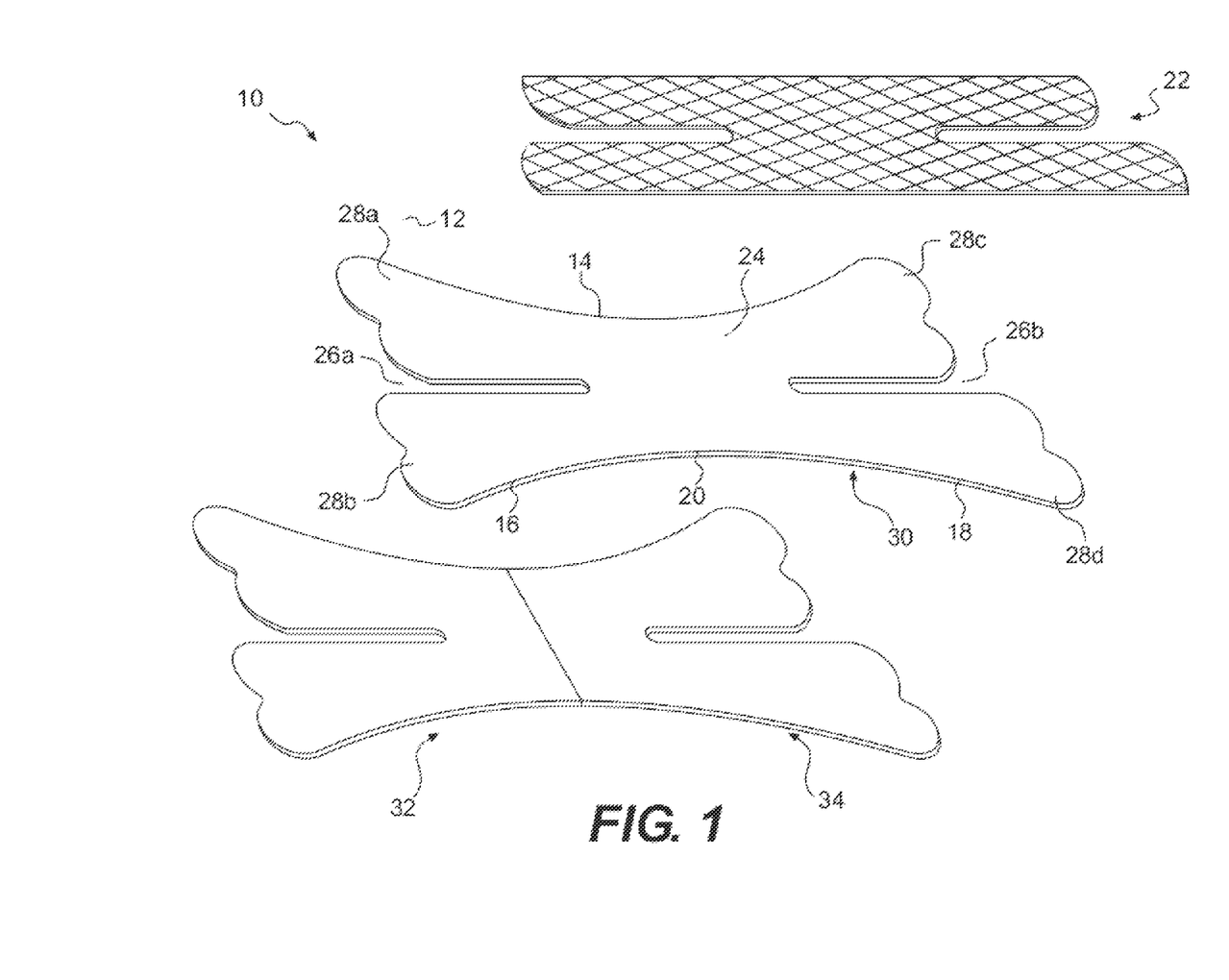
FIG. 1 is an exploded perspective view showing the components of a nasal dilator in accordance with the present invention.
Figure 2:
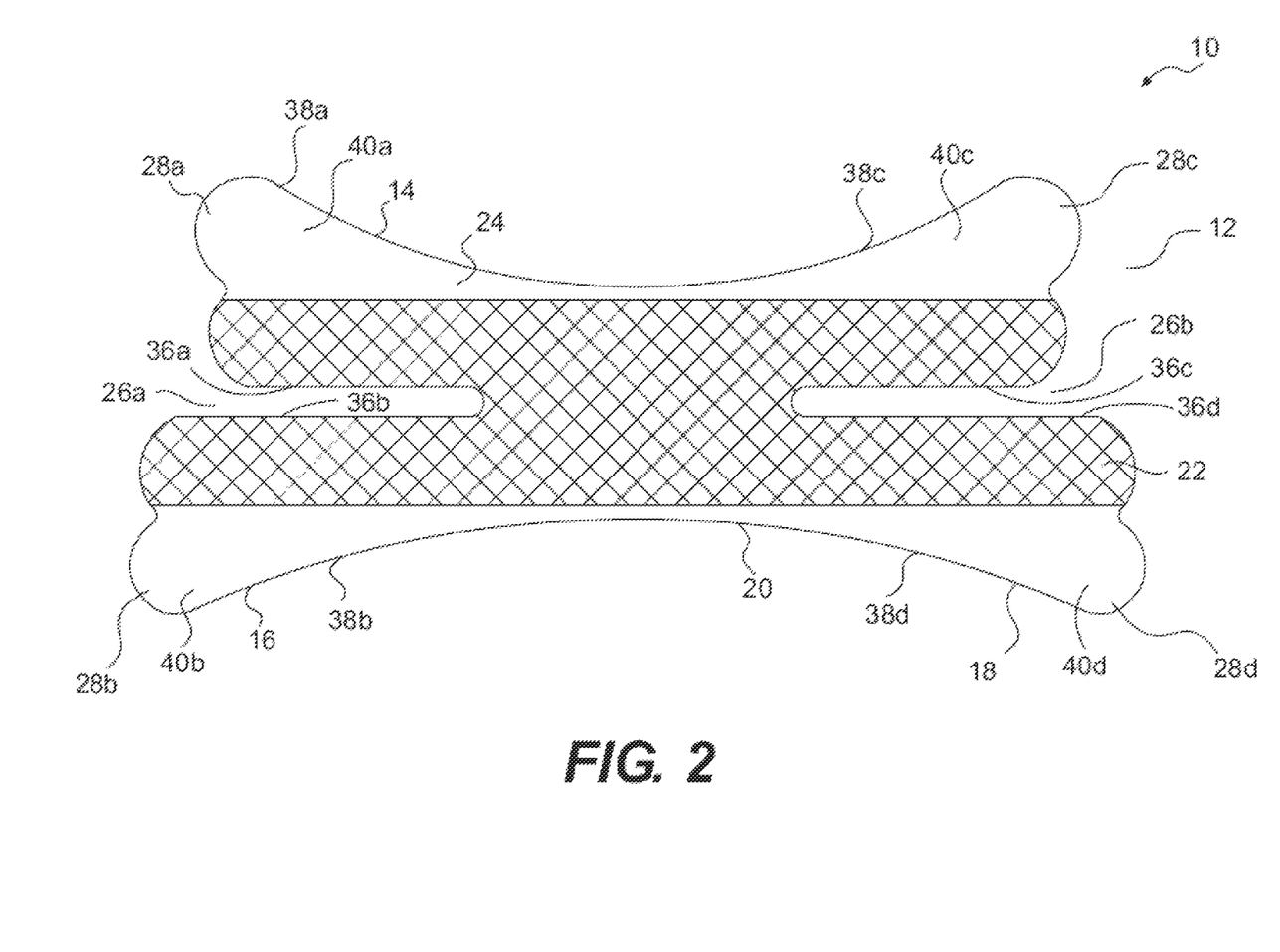
FIG. 2 is a top view of the nasal dilator of FIG. 1.

FIGS. 1 and 2 illustrate an embodiment of the present invention. As can be seen in FIGS. 1 and 2, the nasal dilator 10 comprises a truss member 12, including a flexible strip of material 14, having a first end region 16 and a second end region 18 coupled to the first end region 16 through an intermediate segment 20. The width of the intermediate segment 20 is less than the width of the first and second end regions 16 and 18. The truss member 12 further includes a resilient band 22 secured to a first side 24 of the strip of material 14. The first end region 16 and second end region 18 are divided by slots 26a and 26b to form four resilient branches 28a-28d, slots 26a and 26b being of equal length and width. Resilient branches 28a and 28c are parallel to resilient branches 28b and 28d. Resilient branches 28a-28d have slot side edges 36a-36d and external edges 38a-38d. Resilient band 22 extends to the end of slot side edges 36a-36d. Resilient band 22 does not extend to the end of external edges 38a-38d. Base material 14, however, extends beyond resilient band 22 on external edges to form extended tabs 40a-40d.

As can be seen in FIG. 1, a second side 30 of the strip of material 14 includes a layer of an adhesive substance that extends over the first and second end regions and the intermediate segment. The adhesive substance is bio-compatible with the skin of the nose. Readily removable first and second release liners 32 and 34, cover the first 16 and second 18 end regions and the intermediate segment 20. The first 32 and second 34 release liners cover the adhesive substance and remain in place on the strip of material 14 until the nasal dilator 10 is to be used.

Airflow resistance provided by the nose during breathing is essential as it creates turbulence for preconditioning of the inspired air. The heating, filtering and humidifying that the turbulence in the nasal passageway creates is necessary to promote healthy pulmonary function. In healthy individuals, up to two thirds of the total airway resistance can be attributed to the nasal passageway. Most of this resistance occurs in the region known as the nasal valve which is typically 2 to 3 cm from the anterior opening of the nose. Most of the pulmonary effort in the normal, healthy population is consumed to overcome this resistance during nasal breathing. Nasal breathing is a preferred mode of breathing.

The nasal valve is usually the narrowest part of the nose and is a roughly triangular opening in the anterior portion of the nasal airway formed by the nasal septum, the caudal border of the upper lateral cartilage, the head of the inferior turbinate, and the pyriform aperture and the tissues surrounding it. An external nasal dilator can be utilized to increase the cross sectional area of the nasal valve, decreasing airway resistance, and normalizing or improving pulmonary effort.

Acoustic rhinometry is a diagnostic technique used to assess internal nasal anatomy through analysis of the strength and timing of reflections of a sound pulse introduced via the nostrils. The technique is rapid, reproducible, non-invasive, and requires minimal cooperation from the subject. Through this technique, a graph of nasal cross-sectional area as a function of distance from the nostril is produced, from which the MCA2 and nasal volume of the nasal cavity can be derived. The minimum cross sectional area (MCA2) is the narrowest constriction of the nasal passage found in the anterior 0 to 3 cm portion of the nasal airway, that is, the nasal valve. Nasal volume of the anterior nasal cavity (nasal volume) is the summation of the two-dimensional area measurements from the anterior 0 to 3 cm portion of the nasal passage. In conjunction with the MCA2, the nasal volume provides an additional measure of the passage in the nasal valve area, and is a 3-dimensional measure.

Prototype

A prototype of a nasal dilator of the present invention was constructed. This was a two layer nasal dilator containing flexible piece of base material and a resilient band. The upper, non skin contact, resilient layer is made of 13 mil thick polyester material with an acrylate adhesive. The resilient band is slotted inwardly from both lateral ends, terminating short of the intermediate segment, forming four resilient branches. The slots between the two branches of the springs are typically 0.068 inches wide and 0.631 inches long. The upper resilient element, which includes both upper resilient branches and the adjacent intermediate segment, is 1.963 inches long and typically 0.196 inches wide. The lower resilient element, which includes both lower resilient branches and the adjacent intermediate segment, is 2.286 inches long and typically 0.196 inches wide. The lower, skin contact layer is made of 3 mil thick polyethylene material with an acrylate adhesive and a 63 pound Kraft paper liner. The liner is removed to expose the adhesive for attachment. The two layers are pressed together then cut into the appropriate shape using a continuous flow die cut lamination process.

Nasal Patency Study

A nasal patency study was conducted in 15 normal healthy individuals. The primary objective of this study was to compare the effect of a nasal dilator of the present invention, with four resilient branches, versus the marketed dual band BreatheRight® nasal dilator product on the minimum cross sectional area (MCA2 or nasal valve area) and nasal volume of the nose using acoustic rhinometry. The results are given in Table 1.

This was a single center, randomized, single blind, crossover study of a prototype nasal dilator of the present invention vs. marketed BreathRight® nasal dilator (Tan). Both the marketed BreatheRight® (Tan) and the prototype dilated the nasal valve area (MCA2) in a statistically significant manner compared to baseline, that is, no dilator. An increase in the nasal valve cross sectional area equates to a decrease in nasal resistance and easier nasal breathing. The marketed Tan strip increased dilation by 45% (from 0.95 $cm^2$ to 1.38 $cm^2$) while the prototype increased dilation by 69% (from 0.81 $cm^2$ to 1.37 $cm^2$). Directly comparing the two strips indicates that prototype created 30% more nasal valve cross sectional area than the marketed Tan strip [(0.56−0.43)/0.43*100=30%]. Moreover, both the marketed Tan strip and the prototype increased the volume of the anterior nostril by similar amounts, 31% and 29% respectively.

TABLE 1

Treatment comparisons between a prototype nasal dilator of the present invention and marketed, two-band BreatheRight ® nasal strip (tan) by acoustic rhinometry.

|  | Marketed Tan | Prototype |
| --- | --- | --- |
| MCA2 ($cm^2$) Second Restriction | | |
| Mean baseline | 0.95 | 0.81 |
| Mean with nasal strip in place | 1.38 | 1.37 |
| Mean change from baseline | 0.43* | 0.56** |

TABLE 1-continued

Treatment comparisons between a prototype nasal dilator of the present invention and marketed, two-band BreatheRight ® nasal strip (tan) by acoustic rhinometry.

|  | Marketed Tan | Prototype |
| --- | --- | --- |
| Volume ($cm^3$) (0-3 cm) | | |
| Mean baseline | 4.13 | 4.20 |
| Mean with nasal strip in place | 5.39 | 5.44 |
| Mean change from baseline | 1.26** | 1.23** |

*P-value < 0.05
**P-value < 0.0001

It was surprisingly found that while both strips increased the volume of the nostril similarly, the prototype nasal strip provided a greater increase in nasal valve cross sectional area. Without being bound by theory, it is believed that the prototype, as well as other embodiments of the present invention, provided a greater increase in nasal valve cross sectional area over the dual band BreatheRight® nasal dilator because the prototype, as well as other embodiments of the present invention, pulls the outer wall tissue of the nasal passages in both the outward and upward direction. Nasal dilators known in the art tend to pull in only the outward direction (i.e. orthogonal to the lateral wall of the nose).

Figure 3:
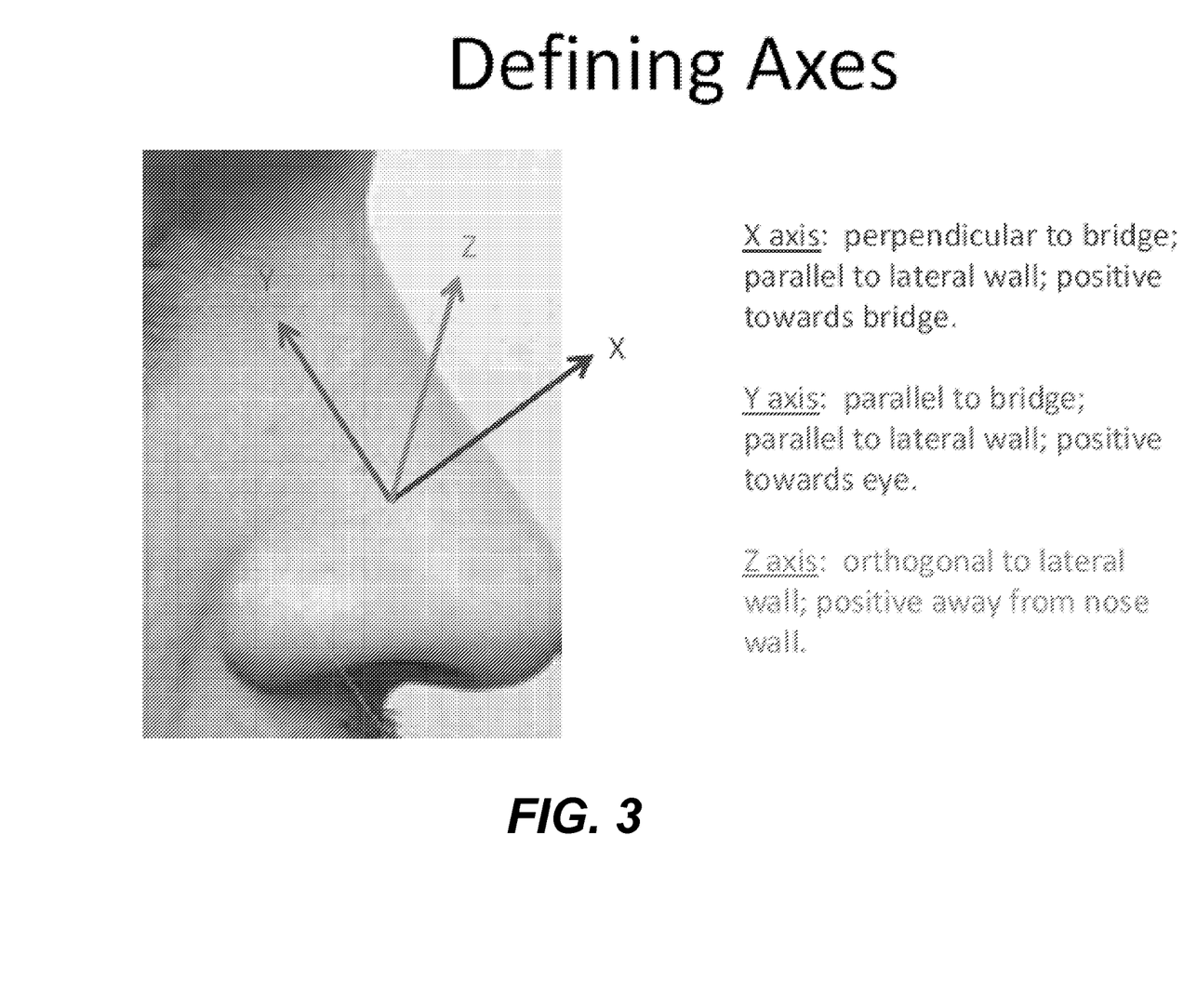
FIG. 3 is a side view of a nose showing a three dimensional coordinate system that can be used to define the lifting forces of external nasal dilators.

The directions of the outward and upward forces are illustrated in FIG. 3. FIG. 3 gives a three dimensional coordinate system that can be used to define the lifting forces of known nasal dilator designs as well as the nasal dilators of the present invention.

The X axis is parallel to the surface of the outside lateral wall of the nose and perpendicular to the bridge of the nose. The positive direction is in the path from the cheek to the bridge.

The Y axis is parallel to the surface of the outside lateral wall of the nose and parallel to the bridge of the nose. The positive direction is in the path from the nostril opening to the eye.

The Z axis is orthogonal to the surface of the outside lateral wall of the nose. The positive direction is outward from the surface of the nose.

The nasal dilators of the present invention pull the outer wall tissues of the nasal passages in both the outward direction (along the positive Z axis) and the upward direction (along the positive X axis).

Figure 4:
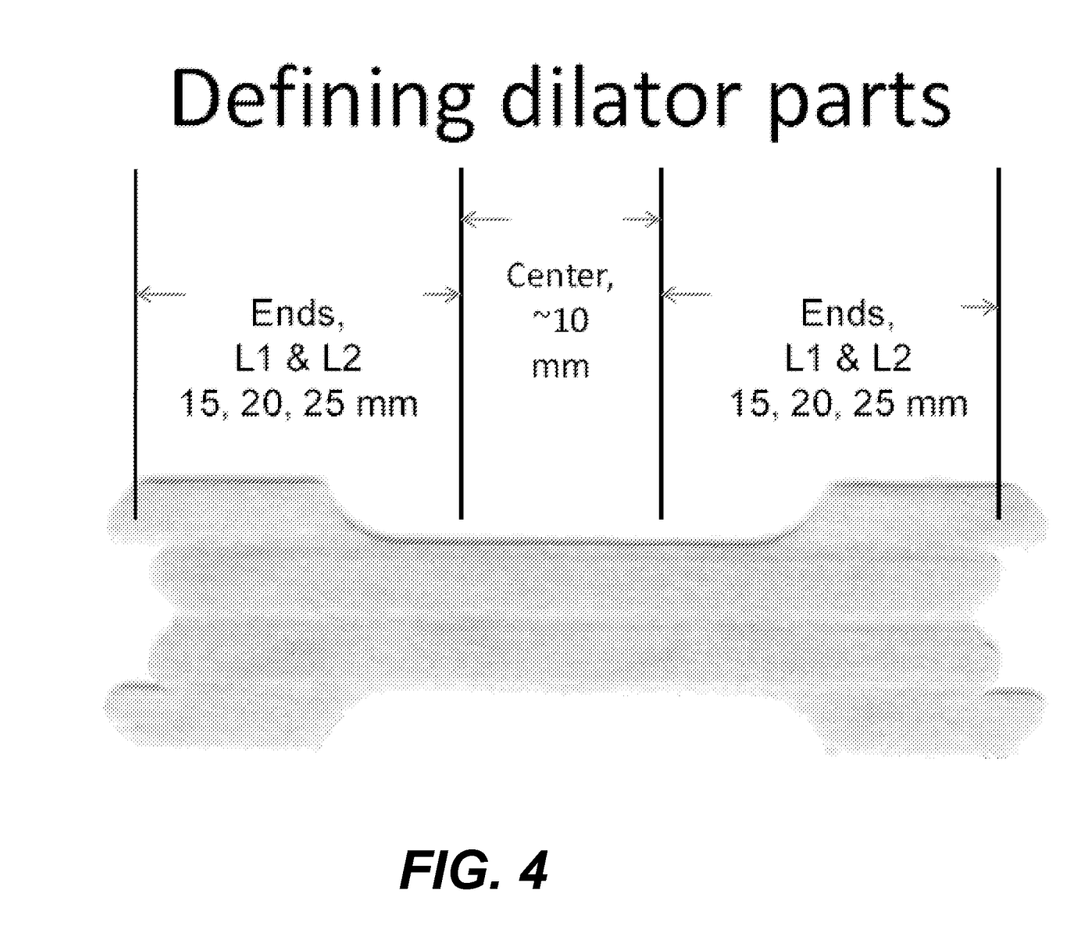
FIG. 4 is a typical external nasal dilator with longitudinal sections shown.

Force vectors can be described to allocate any given force into the three axes, X, Y and Z. FIG. 4 shows a typical dilator with longitudinal sections designated as the center (with approximate length of 10 mm) and the two end regions with lengths varying from 15 to 25 mm. The center portion is typically situated on the flat part of the bridge of the nose while the end regions attach to the outside lateral wall of the nose.

Figure 5:
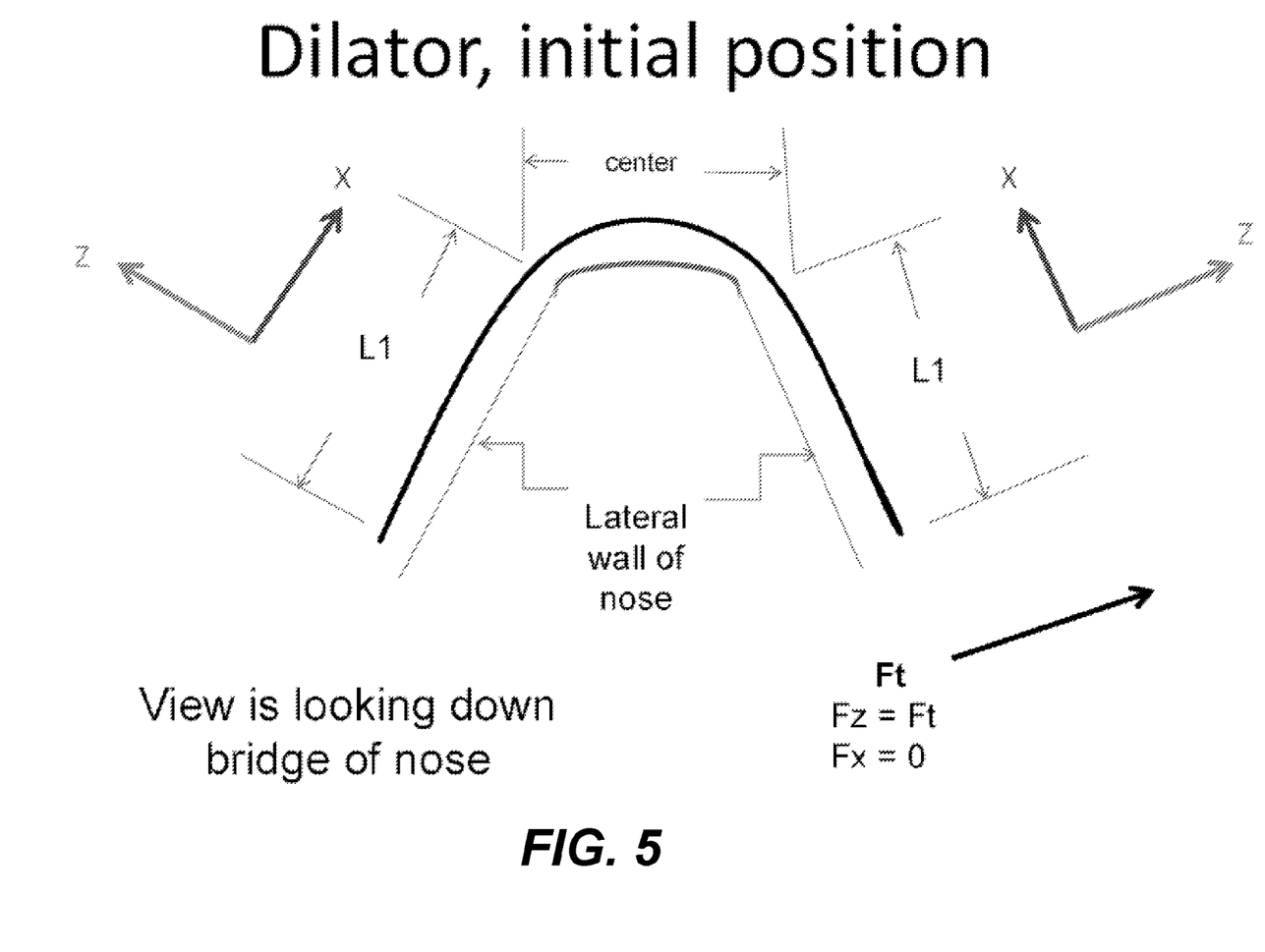
FIG. 5 is an edge view of a nasal dilator attached to the nose but prior to the nasal dilator being released.

FIG. 5 is an edge view of a nasal dilator just as it is attached to the nose but prior to its being "released." "Released" means the time when the spring force of the nasal dilator is allowed to act on the tissue of the nose. It is noted that the plane of the paper is the X-Z plane with the Y axis rising upward from the paper.

The force that the spring exerts on the tissue of the nose is distributed continuously throughout the length, L, in the fashion of a beam. This distributed force can be represented as a single vector force (total force=Ft) that can be separated into force vectors in each of the three axes, X ($F_x$), Y ($F_y$) and Z ($F_z$). The total force, Ft, will have a value of 1.0 in arbitrary units. Initially, prior to "release," the total force vector, Ft, has a direction in the positive Z axis and a value of 1.0. Therefore, Fz=1.0, Fx=0 and Fy=0.

Figure 6:
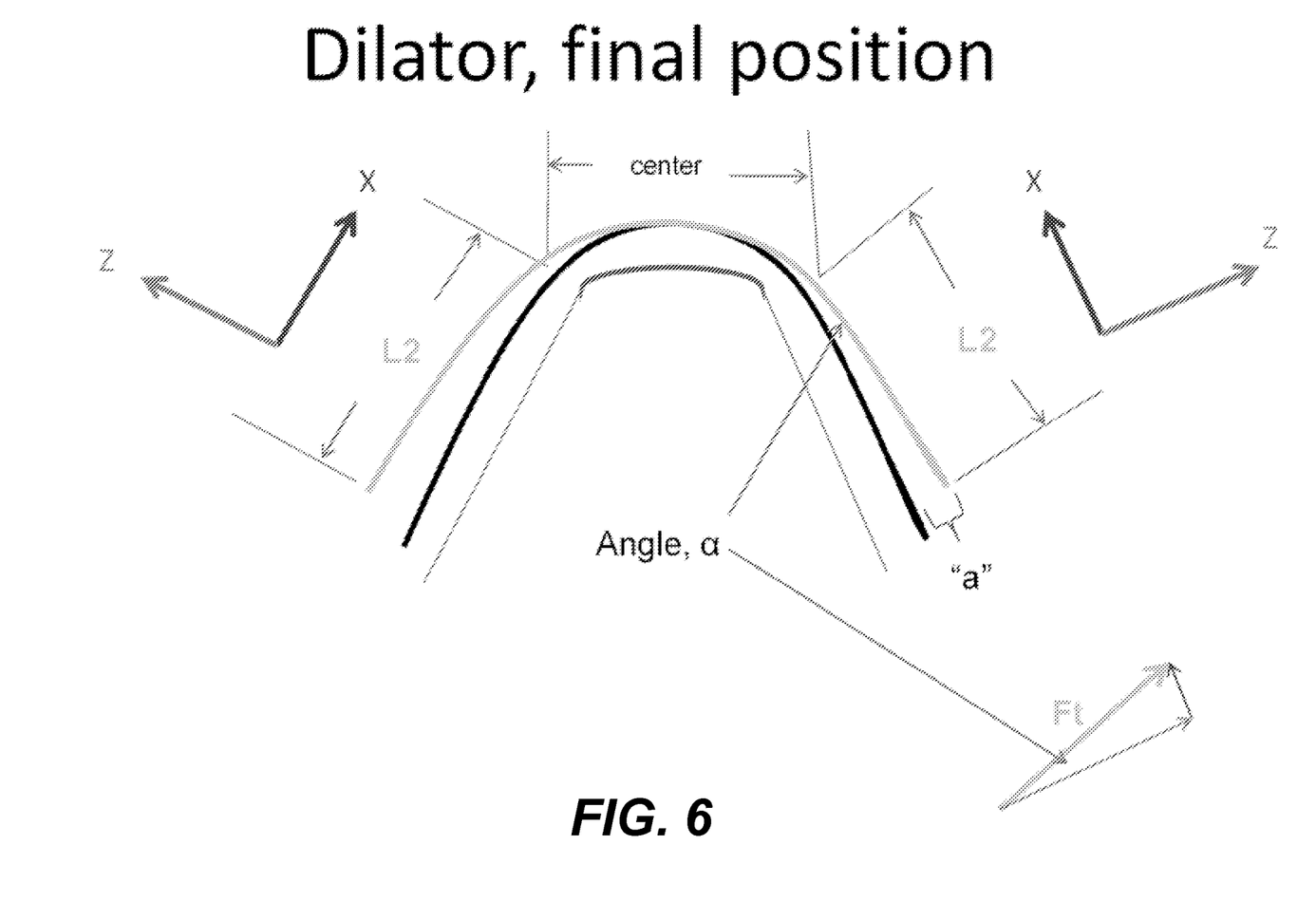
FIG. 6 is an edge view of a nasal dilator attached to the nose after release.

FIG. 6 shows the point after the nasal dilator is "released" where it moves outward pulling the nasal wall tissue with it and dilating the nose. The length L can be seen to pivot through an angle $\alpha$, moving from position L1 to L2. The length, "a," represents the distance moved by the end of the dilator in the Z axis direction. The total force vector, Ft, is still perpendicular to the dilator, L2 but is now at an angle, $\alpha$, to the Z axis. The following relationships result:

Ft=1.0 at an angle, $\alpha$ from the Z axis in the direction of the X axis,
Fy=0,
Fz=Ft*cos($\alpha$),
Fx=Ft*sin($\alpha$), Adding significant force in the positive X direction is thought to add significantly to the dilation achieved with forces in the positive Z axis (or Y axis) direction.

Significant forces in the positive Z axis direction (with insignificant forces in the positive X or Y axis direction) have been shown to dilate nasal passageways, for example the two band BreatheRight® nasal strip. As noted in Johnson U.S. Pat. No. 5,476,091 (column 8, lines 1-14), a minimum force of 5 grams (in the Z axis direction) may produce dilation with a range of useful forces of between 5 and 50 grams. Five grams out of a total of 50 grams of force, or 10%, would be considered significant for nasal dilation purposes. Therefore if a force, Ft, is at an angle, $\alpha$, as shown in FIG. 4, and at least 10% of that force is in the X axis direction it would be considered significant. If the portion of the force in the X axis direction is less than 10% it would not be considered significant.

Table 2 shows the distance that the end of the nasal dilator spring would have to lift (length "a") in order to have at least 10% of the Ft force be present in the Fx (X axis) direction. For example, a 50 mm spring length has to lift as least 2 mm at the end to redirect 10% of its force into the Fx (X axis) direction. The two band BreatheRight® nasal strip does not lift 2 mm in the "a" dimension therefore it redirects an insignificant amount of force (less than 10%) in the X axis direction. This is due to the fact that the springs are generally connected throughout their longitudinal distance restraining their movement in the Z and X axis direction.

TABLE 2

Minimum angle, $\alpha$, and distance "a" required to achieve 10% force in the X axis direction.

| "L1" or "L2" (in mm) | Angle, $\alpha$ (in degrees) | Ft (in a.u.) | Fz (in a.u.) | Fx (in a.u.) | "a" (in mm) |
|---|---|---|---|---|---|
| 15 (40 mm spring length) | 5.8 | 1.00 | 0.99 | 0.10 | 1.5 |
| 20 (50 mm spring length) | 5.8 | 1.00 | 0.99 | 0.10 | 2.0 |
| 25 (60 mm spring length) | 5.8 | 1.00 | 0.99 | 0.10 | 2.5 |

The slotted spring design with four resilient branches of the present invention allows the individual springs to rise sufficiently (distance "a") to provide at least 10% of the total force to be redirected in the X axis direction. Testing has shown that the nasal dilators with this design advantage have demonstrated surprisingly more nasal dilation than would be expected from a comparable strip that did not allow the force to be redirected.

What is claimed is:

1. An external nasal dilator consisting of:
    a first end region adapted to engage the outer wall tissues of a first nasal passage and a second end region adapted to engage the outer wall tissues of a second nasal passage;
    an intermediate segment connecting the first and second end regions and configured to traverse the bridge of the nose located between the first and second nasal passages;
    a flexible strip of base material defining the first and second end regions and the intermediate segment;
    a resilient band traversing the entire length of a first side of the flexible strip of base material;
    an adhesive covering the entire second side of the flexible strip of base material for removably engaging the dilator to the nose of the wearer;
    wherein the dilator including the flexible strip of base material, resilient band and adhesive are slotted inwardly from both lateral ends, terminating short of the intermediate segment, thereby dividing the dilator into four resilient branches comprising two lower branches and two upper branches, each resilient branch having slot side edges wherein the flexible strip of base material, resilient band and adhesive coterminate at the slot side edges and extended tabs, wherein the two upper branches are parallel to the two lower branches along an entire length of a longitudinal axis between the upper and lower branches; wherein each resilient branch further comprises an inwardly slotted portion that forms a first curved surface and a second curved surface, wherein the first curved surface coterminates with the resilient band and the second curved surface extends beyond the length of the resilient band;
    wherein the upper branches are between 15% and 30% shorter than the lower branches.

2. The external nasal dilator of claim 1, wherein the spring force of the resilient band is between about 5 g and about 50 g of force.

3. The external dilator of claim 1, wherein the spring force of the resilient band is between about 18 g and about 28 g of force.

4. The external nasal dilator of claim 1, wherein the outer wall tissues of the nasal passages are pulled by the dilator in both an outward direction and an upward direction.

* * * * *